(12) United States Patent
Derchak

(10) Patent No.: US 8,628,480 B2
(45) Date of Patent: *Jan. 14, 2014

(54) METHODS AND SYSTEMS FOR MONITORING RESPIRATORY DATA

(75) Inventor: P. Alexander Derchak, Summit, NJ (US)

(73) Assignee: adidas AG, Herzogenaurach (DE)

( * ) Notice: Subject to any disclaimer, the term of this patent is extended or adjusted under 35 U.S.C. 154(b) by 400 days.

This patent is subject to a terminal disclaimer.

(21) Appl. No.: 12/976,080

(22) Filed: Dec. 22, 2010

(65) Prior Publication Data

US 2011/0092795 A1 Apr. 21, 2011

Related U.S. Application Data

(63) Continuation of application No. 11/437,335, filed on May 19, 2006, now Pat. No. 7,878,979.

(60) Provisional application No. 60/682,876, filed on May 20, 2005.

(51) Int. Cl.
*A61B 5/08* (2006.01)

(52) U.S. Cl.
USPC .......................... 600/534; 600/529; 600/538

(58) Field of Classification Search
USPC .................................. 600/529–543
See application file for complete search history.

(56) References Cited

U.S. PATENT DOCUMENTS

| | | |
|---|---|---|
| 3,534,727 A | 10/1970 | Roman |
| 3,731,184 A | 5/1973 | Goldberg et al. |
| 3,874,368 A | 4/1975 | Asrican |
| 3,926,177 A | 12/1975 | Hardway, Jr. et al. |
| 4,016,868 A | 4/1977 | Allison |
| 4,033,332 A | 7/1977 | Hardway, Jr. et al. |
| 4,102,331 A | 7/1978 | Grayzel et al. |
| 4,258,718 A | 3/1981 | Goldman |
| 4,267,845 A | 5/1981 | Robertson, Jr. et al. |
| 4,289,142 A | 9/1981 | Kearns |
| 4,306,567 A | 12/1981 | Krasner |
| 4,308,872 A | 1/1982 | Watson et al. |

(Continued)

FOREIGN PATENT DOCUMENTS

| | | |
|---|---|---|
| DE | 4214263 A | 11/1993 |
| EP | 0262778 | 4/1988 |

(Continued)

OTHER PUBLICATIONS

6th Portuguese Conference on Biomedical Engineering, "BioEng' 2001 Conference Papers", (Jun. 2001) 6 pages.

(Continued)

*Primary Examiner* — Michael Kahelin
*Assistant Examiner* — Karen Toth
(74) *Attorney, Agent, or Firm* — Sterne, Kessler, Goldstein & Fox P.L.L.C.

(57) ABSTRACT

This invention provides methods and systems for non-invasively determining the presence (and amount) or absence of dynamic hyperinflation in a subject. The invention is based on a novel combination of respiratory parameters that can be measured in a way that is non-invasive and unobtrusive to the subject. Dynamic hyperinflation is often a significant factor in the quality of life of patients suffering from a variety of obstructive pulmonary diseases, and this invention permits simple, routine tracking and management of dynamic hyperinflation in affected patients.

18 Claims, 7 Drawing Sheets

(56) References Cited

U.S. PATENT DOCUMENTS

Figure 1B:
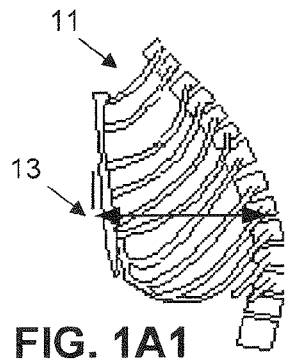
Figure 1B:
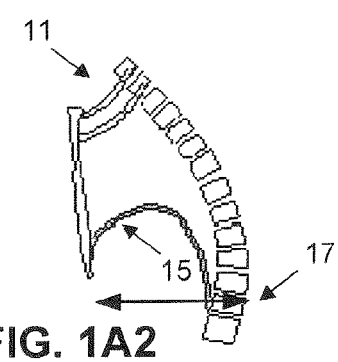
Figure 1B:
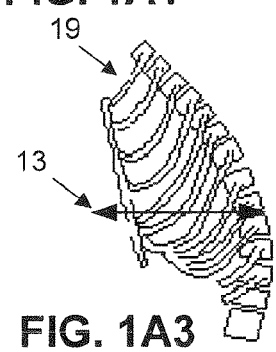
Figure 1B:
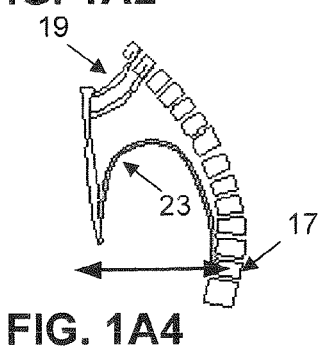
Figure 1B:
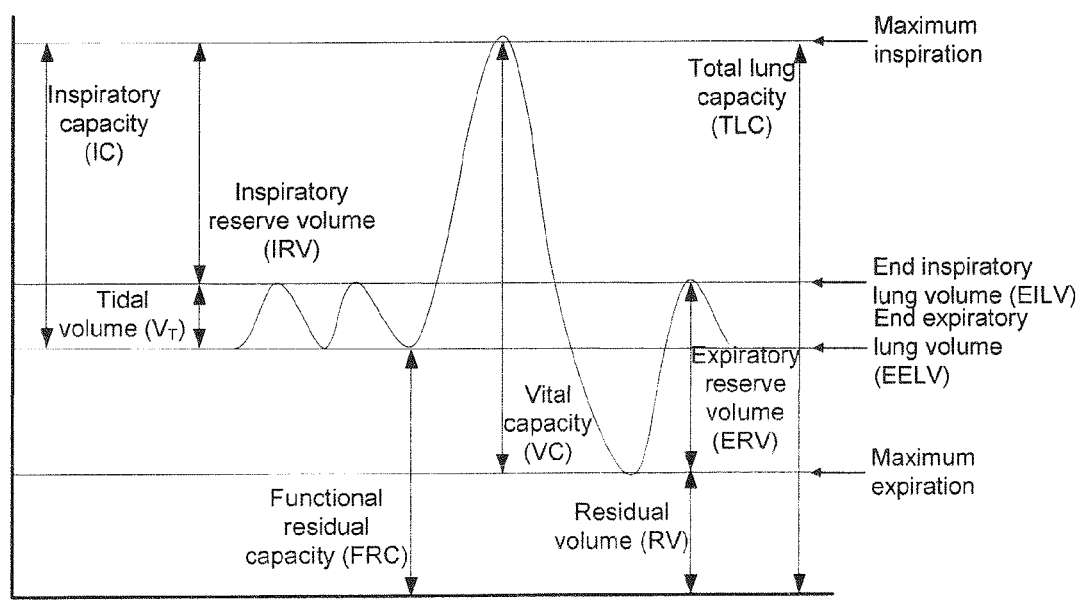

| Patent Number | Date | Inventor |
|---|---|---|
| 4,373,534 A | 2/1983 | Watson |
| 4,387,722 A | 6/1983 | Kearns |
| 4,433,693 A | 2/1984 | Hochstein |
| 4,446,872 A | 5/1984 | Marsoner et al. |
| 4,452,252 A | 6/1984 | Sackner |
| 4,456,015 A | 6/1984 | Sackner |
| 4,463,764 A | 8/1984 | Anderson et al. |
| 4,494,553 A | 1/1985 | Sciarra et al. |
| 4,537,196 A | 8/1985 | Phillipps |
| 4,545,376 A | 10/1985 | Beiter |
| 4,546,777 A | 10/1985 | Groch et al. |
| 4,548,204 A | 10/1985 | Groch et al. |
| 4,549,552 A | 10/1985 | Groch et al. |
| 4,572,197 A | 2/1986 | Moore et al. |
| 4,580,572 A | 4/1986 | Granek et al. |
| 4,648,407 A | 3/1987 | Sackner |
| 4,672,975 A | 6/1987 | Sirota |
| 4,753,088 A | 6/1988 | Harrison et al. |
| 4,777,962 A | 10/1988 | Watson et al. |
| 4,796,639 A | 1/1989 | Snow et al. |
| 4,800,495 A | 1/1989 | Smith |
| 4,807,640 A | 2/1989 | Watson |
| 4,815,473 A | 3/1989 | Watson et al. |
| 4,817,625 A | 4/1989 | Miles |
| 4,819,752 A | 4/1989 | Zelin |
| 4,834,109 A | 5/1989 | Watson |
| 4,860,766 A | 8/1989 | Sackner |
| 4,863,265 A | 9/1989 | Flower et al. |
| 4,867,571 A | 9/1989 | Frick et al. |
| 4,889,131 A | 12/1989 | Salem et al. |
| 4,909,260 A | 3/1990 | Salem et al. |
| 4,911,167 A | 3/1990 | Corenman et al. |
| 4,920,969 A | 5/1990 | Suzuki et al. |
| 4,928,692 A | 5/1990 | Goodman et al. |
| 4,934,372 A | 6/1990 | Corenman et al. |
| 4,955,379 A | 9/1990 | Hall |
| 4,960,118 A | 10/1990 | Pennock |
| 4,966,155 A | 10/1990 | Jackson |
| 4,972,842 A | 11/1990 | Korten et al. |
| 4,981,139 A | 1/1991 | Pfohl |
| 4,986,277 A | 1/1991 | Sackner |
| 5,007,427 A | 4/1991 | Suzuki et al. |
| 5,025,791 A | 6/1991 | Niwa |
| 5,036,857 A | 8/1991 | Semmlow et al. |
| 5,040,540 A | 8/1991 | Sackner |
| 5,074,129 A | 12/1991 | Matthew |
| 5,076,801 A | 12/1991 | Schroll |
| 5,099,841 A | 3/1992 | Heinonen et al. |
| 5,099,855 A | 3/1992 | Yount |
| 5,111,817 A | 5/1992 | Clark et al. |
| 5,131,399 A | 7/1992 | Sciarra |
| 5,143,089 A | 9/1992 | Alt |
| 5,159,935 A | 11/1992 | Sackner et al. |
| 5,173,151 A | 12/1992 | Namose |
| 5,178,151 A | 1/1993 | Sackner |
| 5,224,479 A | 7/1993 | Sekine |
| 5,241,300 A | 8/1993 | Buschmann |
| 5,271,551 A | 12/1993 | Roepke |
| 5,295,490 A | 3/1994 | Dodakian |
| 5,299,120 A | 3/1994 | Kaestle |
| 5,301,678 A | 4/1994 | Wilson et al. |
| 5,329,932 A | 7/1994 | Yount |
| 5,331,968 A | 7/1994 | Williams et al. |
| 5,333,106 A | 7/1994 | Lanpher et al. |
| 5,348,008 A | 9/1994 | Bornn et al. |
| 5,353,793 A | 10/1994 | Bornn et al. |
| 5,416,961 A | 5/1995 | Vinay |
| 5,447,164 A | 9/1995 | Shaya et al. |
| RE35,122 E | 12/1995 | Corenman et al. |
| 5,520,192 A | 5/1996 | Kitney et al. |
| 5,533,511 A | 7/1996 | Kaspari et al. |
| 5,535,738 A | 7/1996 | Estes et al. |
| 5,544,661 A | 8/1996 | Davies et al. |
| 5,564,429 A | 10/1996 | Bornn et al. |
| 5,577,510 A | 11/1996 | Chittum et al. |
| 5,582,337 A | 12/1996 | McPherson et al. |
| 5,584,295 A | 12/1996 | Muller et al. |
| 5,588,425 A | 12/1996 | Sackner et al. |
| 5,601,088 A | 2/1997 | Swanson et al. |
| 5,611,085 A | 3/1997 | Rasmussen |
| 5,617,847 A | 4/1997 | Howe |
| 5,694,939 A | 12/1997 | Cowlings |
| 5,718,234 A | 2/1998 | Warden et al. |
| 5,719,950 A | 2/1998 | Osten et al. |
| 5,720,709 A | 2/1998 | Schnall |
| 5,724,025 A | 3/1998 | Tavori |
| 5,749,365 A | 5/1998 | Magill |
| 5,820,567 A | 10/1998 | Mackie |
| 5,825,293 A | 10/1998 | Ahmed |
| 5,848,027 A | 12/1998 | Dotter |
| 5,882,307 A | 3/1999 | Wright et al. |
| 5,899,855 A | 5/1999 | Brown |
| 5,913,830 A | 6/1999 | Miles |
| 5,921,920 A | 7/1999 | Marshall et al. |
| 5,937,854 A | 8/1999 | Stenzler |
| 5,989,193 A | 11/1999 | Sullivan |
| 5,991,922 A | 11/1999 | Banks |
| 6,002,952 A | 12/1999 | Diab et al. |
| 6,015,388 A | 1/2000 | Sackner et al. |
| 6,018,677 A | 1/2000 | Vidrine et al. |
| 6,035,154 A | 3/2000 | Takahata et al. |
| 6,047,203 A | 4/2000 | Sackner et al. |
| 6,066,093 A | 5/2000 | Kelly et al. |
| 6,067,462 A | 5/2000 | Diab et al. |
| 6,068,568 A | 5/2000 | Kozakura et al. |
| 6,070,098 A | 5/2000 | Moore-Ede et al. |
| 6,120,441 A | 9/2000 | Griebel |
| 6,142,953 A | 11/2000 | Burton et al. |
| 6,145,551 A | 11/2000 | Jayaraman et al. |
| 6,179,786 B1 | 1/2001 | Young |
| 6,198,394 B1 | 3/2001 | Jacobsen et al. |
| 6,223,072 B1 | 4/2001 | Mika et al. |
| 6,254,551 B1 | 7/2001 | Varis |
| 6,261,238 B1 | 7/2001 | Gavriely |
| 6,273,859 B1 | 8/2001 | Remmers et al. |
| 6,287,264 B1 | 9/2001 | Hoffman |
| 6,302,844 B1 | 10/2001 | Walker et al. |
| 6,306,088 B1 | 10/2001 | Krausman et al. |
| 6,341,504 B1 | 1/2002 | Istook |
| 6,361,501 B1 | 3/2002 | Amano et al. |
| 6,381,482 B1 | 4/2002 | Jayaraman et al. |
| 6,413,225 B1 * | 7/2002 | Sackner et al. ............... 600/529 |
| 6,419,636 B1 | 7/2002 | Young et al. |
| 6,436,057 B1 | 8/2002 | Goldsmith |
| 6,443,890 B1 | 9/2002 | Schulze et al. |
| 6,449,504 B1 | 9/2002 | Conley et al. |
| 6,454,719 B1 | 9/2002 | Greenhut |
| 6,461,307 B1 | 10/2002 | Kristbjarnarson et al. |
| 6,463,385 B1 | 10/2002 | Fry |
| 6,478,736 B1 | 11/2002 | Mault |
| 6,483,929 B1 | 11/2002 | Murakami et al. |
| 6,485,431 B1 | 11/2002 | Campbell |
| 6,506,153 B1 | 1/2003 | Littek et al. |
| 6,511,424 B1 | 1/2003 | Moore-Ede et al. |
| 6,513,532 B2 | 2/2003 | Mault et al. |
| 6,551,252 B2 | 4/2003 | Sackner et al. |
| 6,579,231 B1 | 6/2003 | Phipps |
| 6,604,115 B1 | 8/2003 | Gary et al. |
| 6,633,772 B2 | 10/2003 | Ford et al. |
| 6,647,252 B2 | 11/2003 | Smith et al. |
| 6,656,127 B1 | 12/2003 | Ben-Oren et al. |
| 6,687,523 B1 | 2/2004 | Jayaraman et al. |
| 6,699,194 B1 | 3/2004 | Diab et al. |
| 6,702,752 B2 | 3/2004 | Dekker |
| 6,709,402 B2 | 3/2004 | Dekker |
| 6,721,594 B2 | 4/2004 | Conley et al. |
| 6,723,055 B2 | 4/2004 | Hoffman |
| 6,726,636 B2 | 4/2004 | Der Ghazarian et al. |
| 6,727,197 B1 | 4/2004 | Wilson et al. |
| 6,747,561 B1 | 6/2004 | Reeves |
| 6,775,389 B2 | 8/2004 | Harrison et al. |
| 6,783,498 B2 | 8/2004 | Sackner et al. |
| 6,801,916 B2 | 10/2004 | Roberge et al. |
| 6,817,979 B2 | 11/2004 | Nihtila |

(56) References Cited

U.S. PATENT DOCUMENTS

| | | | |
|---|---|---|---|
| 6,858,006 B2 | 2/2005 | MacCarter et al. | |
| 6,881,192 B1 | 4/2005 | Park | |
| 6,941,775 B2 | 9/2005 | Sharma | |
| 6,961,448 B2 | 11/2005 | Nichols et al. | |
| 6,970,731 B1 | 11/2005 | Jayaraman et al. | |
| 6,993,378 B2 | 1/2006 | Wiederhold et al. | |
| 7,001,337 B2 | 2/2006 | Dekker | |
| 7,073,129 B1 | 7/2006 | Robarts et al. | |
| 7,077,810 B2 | 7/2006 | Lange et al. | |
| 7,081,095 B2 | 7/2006 | Lynn et al. | |
| 7,082,327 B2 | 7/2006 | Houben | |
| 7,099,714 B2 | 8/2006 | Houben | |
| 7,104,962 B2 | 9/2006 | Lomask et al. | |
| 7,154,398 B2 | 12/2006 | Chen et al. | |
| 7,207,948 B2 | 4/2007 | Coyle | |
| 7,254,516 B2 | 8/2007 | Case, Jr. et al. | |
| 7,267,652 B2 | 9/2007 | Coyle et al. | |
| 7,319,385 B2 | 1/2008 | Ruha | |
| 7,559,902 B2 | 7/2009 | Ting et al. | |
| 7,604,603 B2 | 10/2009 | Sackner et al. | |
| 7,670,295 B2 | 3/2010 | Sackner et al. | |
| 7,727,161 B2 | 6/2010 | Coyle et al. | |
| 7,762,953 B2 | 7/2010 | Derchak et al. | |
| 7,809,433 B2 | 10/2010 | Keenan | |
| 7,878,979 B2 * | 2/2011 | Derchak | 600/529 |
| 2002/0032386 A1 | 3/2002 | Sackner et al. | |
| 2002/0084130 A1 | 7/2002 | Der Ghazarian et al. | |
| 2002/0090667 A1 | 7/2002 | Ratcliffe et al. | |
| 2002/0123701 A1 | 9/2002 | Eriksen | |
| 2003/0100843 A1 | 5/2003 | Hoffman | |
| 2003/0135097 A1 | 7/2003 | Wiederhold et al. | |
| 2003/0135127 A1 | 7/2003 | Sackner et al. | |
| 2003/0185408 A1 | 10/2003 | Causevic et al. | |
| 2003/0187341 A1 | 10/2003 | Sackner et al. | |
| 2004/0010420 A1 | 1/2004 | Rooks | |
| 2004/0019289 A1 | 1/2004 | Ross | |
| 2004/0030224 A1 | 2/2004 | Sotos et al. | |
| 2004/0111040 A1 | 6/2004 | Ni et al. | |
| 2004/0117204 A1 | 6/2004 | Mazar | |
| 2004/0122334 A1 | 6/2004 | Yamashiro | |
| 2004/0143194 A1 | 7/2004 | Kihara et al. | |
| 2004/0204636 A1 | 10/2004 | Diab et al. | |
| 2004/0210147 A1 | 10/2004 | Houben | |
| 2004/0225227 A1 | 11/2004 | Newman | |
| 2004/0249299 A1 | 12/2004 | Cobb | |
| 2005/0027207 A1 | 2/2005 | Westbrook et al. | |
| 2005/0054941 A1 | 3/2005 | Ting et al. | |
| 2005/0076908 A1 | 4/2005 | Lee et al. | |
| 2005/0119586 A1 | 6/2005 | Coyle et al. | |
| 2005/0125970 A1 | 6/2005 | Nolan | |
| 2005/0211247 A1 | 9/2005 | Noda et al. | |
| 2005/0228234 A1 | 10/2005 | Yang | |
| 2005/0240087 A1 | 10/2005 | Keenan et al. | |
| 2005/0256385 A1 | 11/2005 | Diab et al. | |
| 2006/0000420 A1 | 1/2006 | Davies et al. | |
| 2006/0036183 A1 | 2/2006 | Sackner et al. | |
| 2006/0074334 A1 | 4/2006 | Coyle | |
| 2006/0122528 A1 | 6/2006 | Gal | |
| 2006/0178591 A1 | 8/2006 | Hempfling | |
| 2006/0258914 A1 | 11/2006 | Derchak et al. | |
| 2006/0293609 A1 | 12/2006 | Stahmann et al. | |
| 2007/0027368 A1 | 2/2007 | Collins et al. | |
| 2007/0050715 A1 | 3/2007 | Behar | |
| 2007/0100622 A1 | 5/2007 | Tavares | |
| 2007/0150006 A1 | 6/2007 | Libbus et al. | |
| 2007/0177770 A1 | 8/2007 | Derchak et al. | |
| 2007/0208262 A1 | 9/2007 | Kovacs | |
| 2007/0209669 A1 | 9/2007 | Derchak | |
| 2007/0270671 A1 | 11/2007 | Gal | |
| 2008/0015454 A1 | 1/2008 | Gal | |
| 2008/0027341 A1 | 1/2008 | Sackner et al. | |
| 2008/0045815 A1 | 2/2008 | Derchak et al. | |
| 2008/0051839 A1 | 2/2008 | Libbus et al. | |
| 2008/0082018 A1 | 4/2008 | Sackner et al. | |
| 2008/0221401 A1 | 9/2008 | Derchak et al. | |
| 2008/0269644 A1 | 10/2008 | Ray | |
| 2009/0131759 A1 | 5/2009 | Sims et al. | |
| 2010/0274100 A1 | 10/2010 | Behar et al. | |
| 2011/0009766 A1 | 1/2011 | McCool | |

FOREIGN PATENT DOCUMENTS

| | | |
|---|---|---|
| EP | 0875199 A | 11/1998 |
| GB | 1596298 A | 8/1981 |
| GB | 2116725 | 9/1983 |
| JP | 53126786 A | 6/1978 |
| JP | 58109031 A | 6/1983 |
| JP | 6337933 A | 2/1988 |
| JP | 1091834 A | 4/1989 |
| JP | 5168602 A | 7/1993 |
| JP | 5298589 A | 11/1993 |
| JP | 227383 A | 8/1995 |
| JP | 516253 A | 9/1998 |
| JP | 2001104259 A | 4/2001 |
| WO | WO9810699 | 3/1998 |
| WO | WO0128420 | 4/2001 |
| WO | WO0176467 | 10/2001 |
| WO | WO02060370 | 8/2002 |
| WO | WO02069878 | 12/2002 |
| WO | WO03022149 | 3/2003 |
| WO | WO2004019503 | 3/2004 |
| WO | WO2005115242 | 12/2005 |
| WO | WO2006002338 | 1/2006 |
| WO | WO2006009830 | 1/2006 |
| WO | WO2007089751 | 2/2007 |
| WO | WO2007090111 | 6/2007 |
| WO | WO2007089751 | 8/2007 |
| WO | WO2009074973 | 6/2009 |
| WO | WO2010027515 | 3/2010 |

OTHER PUBLICATIONS

Aliverti, et al., "Chronic Obstructive Pulmonary Disease: Regional Chest Wall Volumes During Exercise in Chronic Obstructive Pulmonary Disease." *Thorax*, 59:210-216, 7 pages, 2004.

Almeida et al., "Wavelet Transform Based Matlab System for the Detection and Delineation of QRS Complexes in Ambulatory ECG Recordingd", *6th Portuguese Conference on Biomedical Engineering* (Jun. 2001), 2 pages.

Anderer et al., "Artifact Processing in Computerized Analysis of Sleep EEG—A Review" *Neuropsychobiology*, 40:150-157 (1999), 8 pages.

Bianchi et al., "Extraction of the Respiration Influence From the Heart Rate Variability Signal by Means of Lattice Adaptive Filter", *IEEE Transactions on Biomedical Engineering*, pp. 121-122 (1994), 2 pages.

National Biometric Test Center, "The Functions of Biometric Identification Devices", *San Jose State University Biometrics Publications*, www.engr.sjsu.edu/biometrics/publications_tech.html (printed Jul. 28, 2005), 25 pages.

National Biometric Test Center, "Biometric Technology—Testing, Evaluation, Results", *San Jose State University Biometrics Publications*, www.engr.sjsu.edu/biometrics/publications_tech.html (printed Jul. 28, 2005), 13 pages.

Blechert et al., "Identifying Anxiety States Using Broad Sampling and Advance Processing of Peripheral Physiological Information," *Psychosom Med Dec. 2007*; 935-43 Epub Nov. 8, 2007, 6 pages.

Bloch et al., "Specific respiratory patterns distinguish among human basic emotions," *International Journal of Psychophysiology*, 11:141-154 (1991), 14 pages.

Bonnet et al., "EEG Arousals: Scoring Rules and Examples, A Preliminary Report from the Sleep Disorders Atlas Task Force of the American Sleep Disorders Assocation," *Sleep*, 152(2): 173-184 (1992), 12 pages.

Brack, "Cheyne-Stokes respiration in patients with congestive heart failure," Swiss Med Weekly 133:605-610 (2003), 7 pages.

Costa et al., "Multiscale Entropy Analysis of Complex Physiologic Time Series," Physical Review Letters 89(6):068102-1-4 Aug. 5, 2002, 4 pages.

(56) References Cited

OTHER PUBLICATIONS

Coyle et al., "Home Measurement of Cough Indicates Circadian Frequency Pattern and Abnormal Distribution During Sleep," LifeShirt System, study sponsored by Pfizer, Inc., Jun. 2004, 1 page.
Fahrenberg, "Origins and Developments of Ambulatory Monitoring and Assessment," (2001), 30 pages.
Gore Electronic Products, "Expanded PTFE Insulation Material", www.goreelectronics.com (visited Aug. 2005), 4 pages.
Grossman et al., "Reliability of Respiratory Tidal Volume Estimation by Means of Ambulatory Inductive Plethysmography," Biomed Sci Instrum 42:193-8 (2006), 6 pages.
Grossman et al., "A Comparison of Three Quantification Methods for Estimation of Respiratory Sinus Arrhythmia", Psychophycology, 27(6):702-714 (1900), 17 pages.
Istepanian et al., "Microcontroller-Based Underwater Acoustic ECG Telemetry System", IEEE Transactions on Information Technology in Biomedicine, 1(2):150-154 (Jun. 1997), 5 pages.
Keenan et al., "Adaptive Filtering of Heart Rate Signals for an Improved Measure of Sympathovagal Balance," Jan. 1, 2005, 8 pages.
Klabunde, "Electrocardiogram (EKG, ECG)", Cardiovasular Physiology Concepts, www.cvphysiology.com (visited Mar. 2005),3 pages.
Lake et al., "Sample entropy analysis of neonatal heart rate variability," Am J Physiol Regul Integr Comp 283:R789-97 (2002), 10 pages.
Marin et al., "Inspiratory Capacity, Dynamic Hyperinflation, Breathlessness, and Exercise Performance During the 6-Minute-Walk Test in Chronic Obstructive Pulmonary Disease", Am. J. Respir. Crit. Care Med., vol. 163., pp. 1395-1399, (2001), 5 pages.
McCool et al., "Estimates of ventilation from body surface measurements in unstricted subjects," J. Appl. Physiol. 61(3):1114-9 (1986), 6 pages.
McCool et al., "Tidal Volume and Respiratory Timing Derived From a Portable Ventilation Monitor," Chest 122:684-91 (2002), 10 pages.
McNaughton et al., "Metallized Polymer Fibers as Leadwires and Intrafascicular Microelectrodes", J. Neurosci. Methods, 70(1):103-10 (1996), 2 pages.
Micro-Coax, "About Micro-Coax", www.micro-coax.com (visited Aug. 2004), 9 pages.
Niskanen et al., "Software for Advanced HRV Analysis", University of Kuopio Department of Applied Physics Report Series, pp. 1-11 (Feb. 2002), 12 pages.
O'Donnell, "Ventilatory Limitations in Chronic Obstructive Pulmonary Disease", Medicine & Science in Sports & Exercise, pp. S647-S655, (2001), 9 pages.
O'Donnell et al., "Dynamic Hyperinflation and Exercise Intolerance in Chronic Obstructive Pulmonary Disease", Am. J. Respir. Crit. Care Med., 164:770-777 (2001), 8 pages.
Park et al., "Automated Detection and Elimination of Periodic ECG Artifacts in EEG Using the Energy Interval Histogram Method", IEEE Transactions on Biomedical Engineering 49(12):1526-1533 (2002),8 pages.
Pietraszek et al., "Simple Telemetry System for ECG Recording", Polish J. Med. Phys. & Eng. 2002; 8(3): 193-198, 4 pages.
Rampil, "A Primer for EEG Signal Processing in Anesthesia," Anesthesiology 89(4):980-1002 Oct. 1998, 15 pages.
Richman et al., "Physiological time-series analysis using approximate entropy and sample entropy," Am. J. Physiol Circ Physiol 278:H2039-49 (2000), 11 pages.
Signal Consulting Inc., "Inductance of Circular Loop", www.sigcon.com (visited Aug. 2005), 2 pages.
Sijbers et al., "Reduction of ECG and gradient related artifacts in simultaneously recorded human EEG/MRI data,", Magnetic Resonance Imaging 18:881-6 (2000), 6 pages.
Snyder et al., "Ventilatory Responses to Hypoxia and High Altitude During Sleep in Aconcagua Climbers," Wilderness and Environmental Medicine 18:138-145 (2007), 8 pages.
Szabo et al., "Prognostic Value of Heart Rate Variability in Chronic Congestive Heart Failure Secondary to Idiopathic or Ischemic Dilated Cardiomypathy," Am J Cardiol. 79:978-980 (1997), 3 pages.

van Dijk et al., "Determinants of Brachial Artery mean 24 h PulsePressure in Individuals with Type II diabetes mellitus and untreated mild hypertension", Clinical Science (2002), 102, pp. 177-186, 10 pages.
Vogiatzis, et al., "Respiratory Kinematics by Optoelectronic Plethysmography During Exercise in Men and Women.", Eur J of App Physiol, 581-587, 7 pages, 2004, 7 pages.
Wachowski, Andy and Larry, The Matrix, released Mar. 31, 1999 by Warner Bros. Pictures, see 1:26:29, 2:03:10, and 2:04:41, 13 pages.
Wilhelm et al., "Distinguishing Emotional From Physical Activation in Ambulatory Psychophysiological Monitoring," Biomed Sci Instrum 42:458-63 (2006), 6 pages.
Wilhelm et al., "Taking the laboratory to the skies: Ambulatory assessment of self-report, autonomic, and respiratory responses in flying phobia," Psychophysiology 35:596-606 (1998), 11 pages.
Supplementary Partial European Search Report of the European Patent Office, Application No. EP 06784447.2, dated Jan. 20, 2010, 9 pages.
Supplementary Partial European Search Report of the European Patent Office, Application No. EP 04759405.6, dated Jan. 25, 2011, 4 pages.
International Search Report and the Written Opinion of the International Searching Authority, application No. PCT/US2008/061171, dated Nov. 14, 2008, 10 pages.
International Search Report and the Written Opinion of the International Searching Authority, application No. PCT/US06/60264, dated Jan. 15, 2008, 8 pages.
International Search Report and the Written Opinion of the International Searching Authority, application No. PCT/US2007/82688, dated May 8, 2008, 7 pages.
International Search Report and the Written Opinion of the International Searching Authority, application No. PCT/US2008/072414, dated Nov. 12, 2008, 7 pages.
Extended European Search Report for Application No. EP 07798146.2, Applicant: adidas AG, mailed Oct. 19, 2010.
Extended European Search Report for Application No. EP 10174873.9, Applicant: adidas AG, mailed Dec. 8, 2010.
Extended European Search Report for Application No. EP 10174680.8, Applicant: adidas AG, mailed Dec. 9, 2010.
Extended European Search Report for Application No. EP 10174876.2, Applicant: adidas AG, mailed Dec. 9, 2010.
Extended European Search Report for Application No. EP 10174881.2, Applicant: adidas AG, mailed Dec. 9, 2010.
Extended European Search Report for Application No. EP 10174683.2, Applicant: adidas AG, mailed Dec. 27, 2010.
Partial European Search Report for Application No. EP 10174885.3, Applicant: adidas AG, mailed Jan. 4, 2011.
Office Action dated Nov. 30, 2010 from Japanese Appl. No. 2006-509897, Adidas AG, Systems and Methods for Respiratory Event Detection, with translation.
Office Action dated Aug. 2, 2010 from U.S. Appl. No. 11/373,822, Sackner, System and Methods for Ambulatory Monitoring of Physiological Signs, filed Mar. 9, 2006.
Office Action dated Sep. 28, 2010 from U.S. Appl. No. 11/503,350, Behar, Systems and Methods for Monitoring Subjects in Potential Physiological Distress, Aug. 10, 2006.
Office Action dated Oct. 15, 2010 from U.S. Appl. No. 11/627,198, Derchak, System and Method for Identity Confirmation Using Physiologic Biometrics to Deteimine a Physiologic Fingerprint, filed Jan. 25, 2007.
Office Action dated Nov. 18, 2010 from U.S. Appl. No. 11/492,484, Behar, Computer Interfaces Including Physiologically Guided Avatars, filed Jul. 24, 2006.
Office Action dated Jan. 4, 2011 from U.S. Appl. No. 11/233,317,Gal, Improved Sensors for Inductive Plethysmographic Monitoring Applications and Apparel Using Same, Sep. 21, 2005.
Office Action dated Jan. 27, 2011 from U.S. Appl. No. 10/991,877, Keenan, Method and system for processing data from ambulatory physiological monitoring, Nov. 18, 2004.
Office Action dated Feb. 2, 2011 from U.S. Appl. No. 11/373,822, Sackner, Systems and methods for ambulatory monitoring of physiological signs, Mar. 9, 2006.

(56) References Cited

OTHER PUBLICATIONS

U.S. Appl. No. 13/357,772, Sackner, System and Methods for Ambulatory Monitoring of Physiological Signs, filed Feb. 17, 2006.

U.S. Appl. No. 11/373,822, Sackner, System and Methods for Ambulatory Monitoring of Physiological Signs, filed Mar. 9, 2006.

U.S. Appl. No. 12/869,576, Stone, Method and System for Limiting Interference in Magnetometer Fields, filed Aug. 26, 2010.

U.S. Appl. No. 12/869,578, Derchak, Noninvasive Method and System for Monitoring Physiological Characterisitics, filed Aug. 26, 2010.

U.S. Appl. No. 12/869,582, Derchak, Noninvasive Method and System for Monitoring Physiological Characteristics and Athletic Performance, filed Aug. 26, 2010.

U.S. Appl. No. 12/869,585, Derchak, Noninvasive Method and System for Monitoring Physiological and Athletic Performance Characteristics of a Subject, filed Aug. 26, 2010.

U.S. Appl. No. 12/869,586, Derchak, Physiological Database and System for Population Modeling and Method of Population Modeling, filed Aug. 26, 2010.

U.S. Appl. No. 12/869,592, Derchak, Multimodal Method and System for Transmitting Information About a Subject, filed Aug. 26, 2010.

U.S. Appl. No. 12/869,625, Derchak, Method and System for Interpretation and Analysis of Physiological, Performance, and Contextual Information, filed Aug. 26, 2010.

U.S. Appl. No. 12/869,627, Derchak, Physiological Monitoring Garment, filed Aug. 26, 2010.

U.S. Appl. No. 12/872,174, Derchak, Physiological Monitoring Garment, filed Aug. 31, 2010.

U.S. Appl. No. 12/971,193, Sackner, Systems and Methods for Ambulaory Monitoring of Physiological Signs, filed Dec. 17, 2010.

U.S. Appl. No. 12/976,080, Derchak, Methods and Systems for Monitoring Respiratory Data, filed Dec. 22, 2010.

\* cited by examiner

METHODS AND SYSTEMS FOR MONITORING RESPIRATORY DATA

CROSS REFERENCE TO RELATED APPLICATIONS

This application is a continuation of U.S. nonprovisional application Ser. No. 11/437,335, filed May 19, 2006, which claims the benefit of prior U.S. provisional application 60/682,876 filed May 20, 2005. The disclosures of U.S. application Ser. Nos. 11/437,335 and 60/682,876 are hereby incorporated by reference in their entirety.

1. FIELD OF THE INVENTION

The present invention relates to determination of pulmonary parameters of individuals, especially pulmonary parameters of patients with obstructive pulmonary diseases. More particularly, this invention provides systems and methods that measure dynamic hyperinflation using methods that require little if any patient attention.

2. BACKGROUND OF THE INVENTION

Chronic obstructive pulmonary disease (COPD) and other diseases with a similar physiological defects (e.g., acute and chronic asthma) are of considerable clinical interest since they are important worldwide causes of morbidity and mortality. Cardinal symptoms of these diseases include sensations of dyspnea or breathlessness as well as other respiratory discomforts. These occur on exertion, and in advanced disease also at rest. Briefly, these symptoms are due to progressive loss of lung volume available for active breathing as the lung becomes filled with more and more air trapped ("hyperinflation") behind airways that have increasing expiratory flow limitations. The airway expiratory flow limitations result from the pathology underlying these diseases that, for example, causes blockages within airways (e.g., by increased mucus) or partial airway collapse (e.g., by decreased tethering due to parenchymal destruction). The increase in lung volume changes the pressure-volume relationship of the chest-wall, reducing the efficiency of the respiratory musculature.

Pathologically, COPD is a heterogeneous disorder characterized by expiratory flow limitations usually due to narrow, easily collapsed airways. When arising from emphysema or chronic bronchitis, parenchymal and vascular destruction reduces lung recoil and airway tethering leading to expiratory collapse of small and large airways. Acute and chronic asthma, along with chronic bronchitis, can also cause expiratory flow limitation by airway narrowing due to bronchial hypertrophy, bronchial spasm, and increased viscid secretions into the bronchi. Pulmonary diseases characterized by prominent expiratory air flow limitations are generically referred to herein as "obstructive pulmonary diseases" (OPD).

It is common during the course of these diseases that periods of acutely increased hyperinflation ("dynamic hyperinflation") are superimposed on the chronic underlying and often slowly progressive hyperinflation. Dynamic hyperinflation (abbreviated as "DH") is associated with periods of increased drive to breathe which can be due to exercise ("exercise dyspnea"), excitement, pulmonary infections, waking in the morning, and numerous other factors. The additional hyperinflation caused by DH can even further decrease lung capacity available for active breathing, and therefore can be a substantial factor in the experience of patients with COPD and similar diseases, negatively impacting their functional capacity and quality of life.

Thus, it is clinically advantageous to track and treat episodes of DH to the extent possible. In the prior art, DH has usually been tracked by serial measurements of inspiratory capacity (abbreviated herein as "IC") requiring a patient to perform a specific breathing maneuver at rest while, for example, breathing into a spirometer or breathing while inside a calibrated pneumo-tachographic chamber. The specific maneuver requires that the patient must, first, repeatedly inspire and expire in a relaxed manner, and then must inspire maximally and resume normal breathing. The IC is difference between the last inspiratory volume and the last tidal expiratory volume. Preferably, this maneuver is repeated until two or more consistent IC values are obtained.

This requirements of this measurement technique can distort IC measurements, and thus confound identification and measurement of DH also. A patient must interrupt whatever they were doing and then consciously attend to and perform a specific breathing sequence while using instrumentation that is at best cumbersome. The large inspiration required by IC measurement can be unpleasant, and may actually trigger a period of hyperinflation. Performance of the IC maneuver is especially intrusive during exercise, and measurements of DH precipitated by exercise ("exercise dyspnea") are likely to be more confounded than are measurement of other forms of DH.

The prior art lacks systems and methods for measuring DH that require little or no attention by a patient. Such methods and system would be useful for, e.g., assessing and managing COPD and other lung diseases.

A number of references are cited herein, the entire disclosures of which are incorporated herein, in their entirety, by reference for all purposes. Further, none of these references, regardless of how characterized above, is admitted as prior to the invention of the subject matter claimed herein.

3. SUMMARY OF THE INVENTION

The objects of this invention include methods and systems that assess dynamic hyperinflation ("DH") in a patient unobtrusively, that is with little or no attention by the patient, and also preferably non-invasively, that is permitting the patient to perform normal daily activities. Tracking and managing DH using this invention can be useful in improving the quality of life of patients with obstructive pulmonary diseases ("OPD"), because DH can be a substantial factor in their disease experience. OPD patients include patients with obstructive pulmonary diseases, e.g., COPD, chronic bronchitis, emphysema, chronic or acute asthma, and other diseases with similar physiological effects.

This invention is based on the inventor's discovery that the presence or absence of DH and its amount (e.g., the volume of dynamically retained air) can be assessed by a novel combination of respiratory parameters. In particular, patterns of changes in the median rib cage contribution to tidal volume (M % RC when measured in percent) and the median absolute value of changes in end-expiratory lung volume (MqdEELV) can reliably detect DH. During periods of increased respiratory demand, e.g., during exercise, these parameters often increase together in normal patients who do not have DH. In other normal patients, one of these parameters may change while the other does not change, or neither of these parameters may change. In contrast, OPD patients experiencing DH during periods of increased respiratory demand demonstrate a different and unique pattern in which MqdEELV increases while M % RC decreases. These different patterns of changes of MqdEELV and M % RC reliably discriminate patients who experience DH from those who do not. As used here, a parameter "changes" (or "increases" or "decreases") if its values, or if an average, or median, or mode, or other statistical measure of its values, observed in two conditions differ to a statistically meaningful degree.

This invention provides methods and programmed computer systems that implement this discovery. These methods and systems receive respiratory data sufficient to determine MqdEELV and M % RC, process this data, and output assessments of the presence or absence of DH and optionally of its amount. Various preferred embodiments of this inventor are more or less specifically directed to different patient measurement environments, e.g., hospital environments, clinical environments, ambulatory environments, laboratory environments, and the like. Specifically, the various embodiments are adapted to accept respiratory data from the different respiratory sensors found in these different environments, and are implemented on the various types of computers also found in these different environments, from computers with limited portability to portable computers that can be carried by a patient.

One preferred embodiment is directed to ambulatory patients. As used herein "ambulatory environment" (or "ambulatory"), is taken to means an environment that permits patients to engage their normal daily activities in a substantially unconstrained manner. In this embodiment, respiratory data is measured using sensors configured on and/or carried by a comfortable wearable item. Preferred respiratory sensors measure sizes of the patient's torso at one or more levels, e.g., at a rib cage level and/or and abdominal level, using plethysmographic technologies, particularly inductive plethysmographic technologies. Data is processed either by portable processing devices that can be carried by the patient or by remote computer systems at least to extract tidal volume ($V_T$) from sensor data and then to determine MqdEELV and M % RC from $V_T$ data. DH is then assessed in dependence one the latter two parameters. Processed and/or raw respiratory data is preferably transmitted from local devices to remote systems using means that permit a patient to carry out their normal activities with little or no significant constraint. For example, data can be transmitted wirelessly, or physically transferred on computer readable media.

Specifically, "plethysmography" and its derivative words, as used herein, refer to an externally-determined (non-invasive) measurement of a size of a body part. Also, "inductive plethysmography", as used herein, is a plethysmographic measurement based on determination of an inductance or a mutual inductance of conductive elements arranged on the body part. A "plethysmographic signal" is a signal generated by plethysmography, and usually by inductive plethysmography. The part of the body measured by plethysmography may include, singly or in combination, one or more portions of the chest, abdomen, neck, arm, or the like.

The present invention also includes computer readable mediums, both for long term storage and for portable storage, which are configured with encoded instructions for causing a processor to perform the methods of this invention and/or with raw or processed data used by these methods.

Specific embodiments of this invention will be appreciated from the following detailed descriptions, appended claims, and attached figures.

4. BRIEF DESCRIPTION OF THE DRAWINGS

Figure 2:
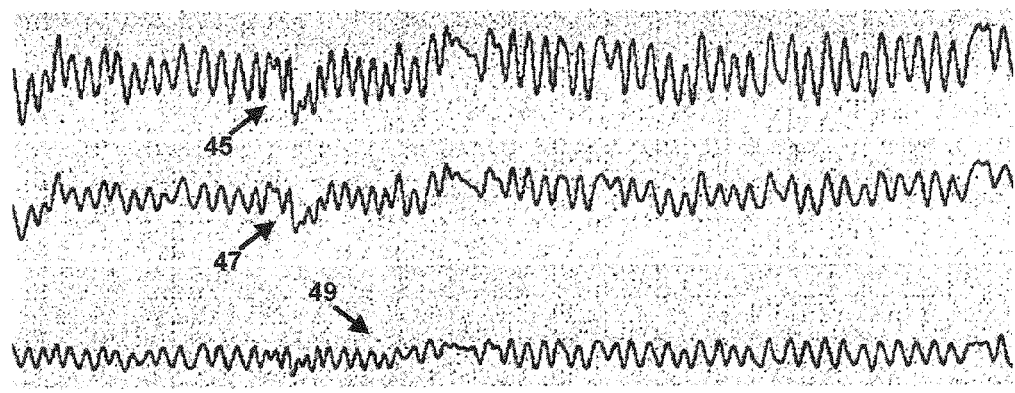
Figure 3:
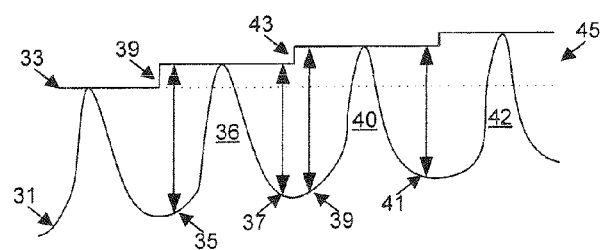
Figure 4:
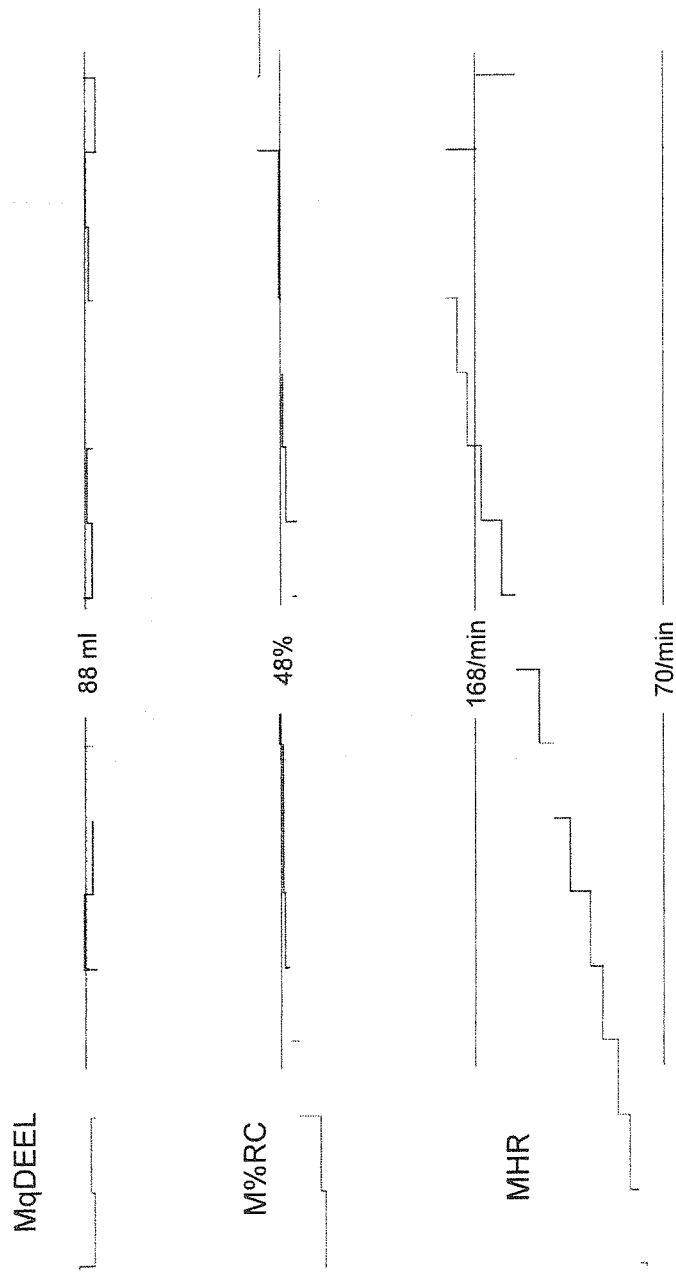
Figure 5:
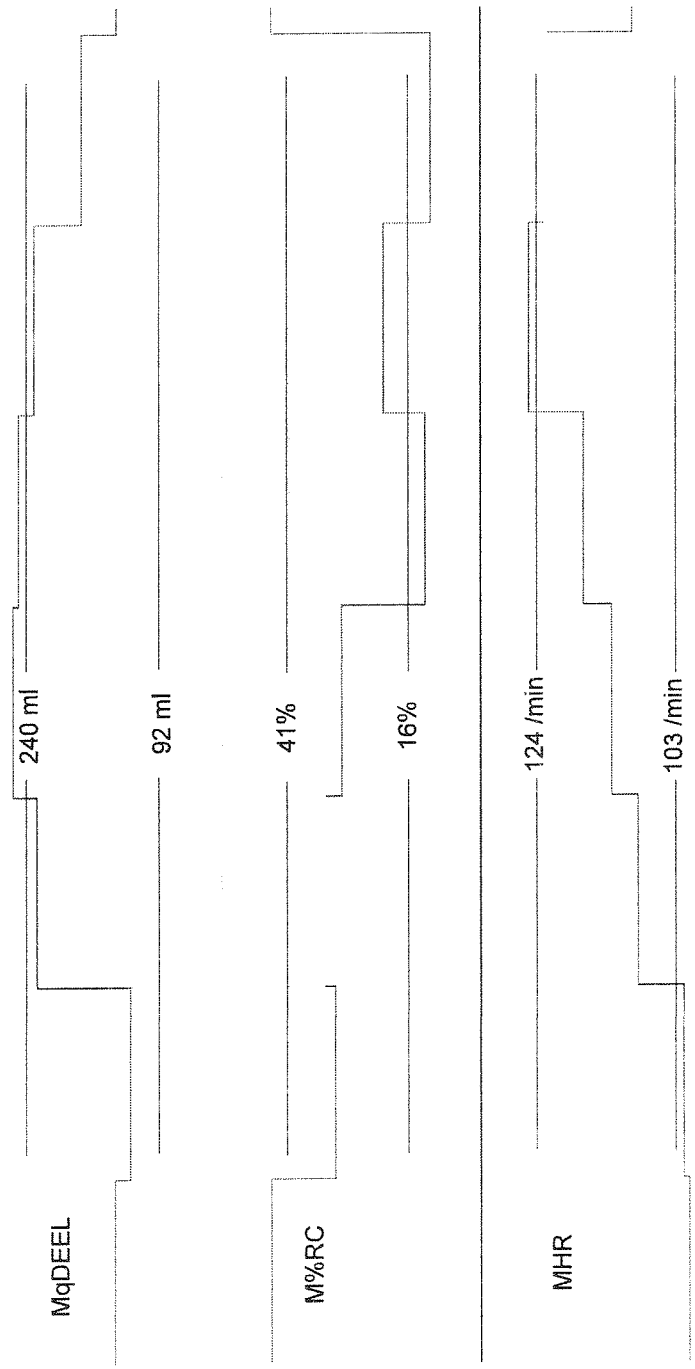
Figure 6A:
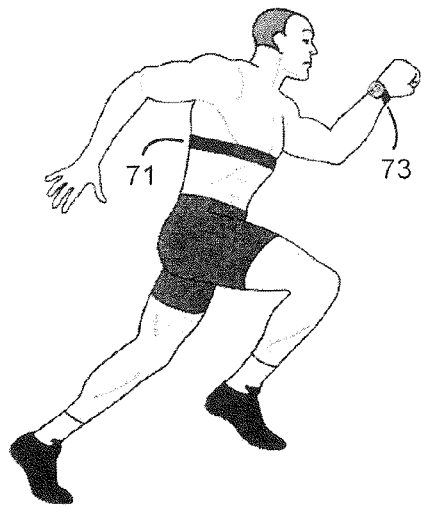
Figure 6B:
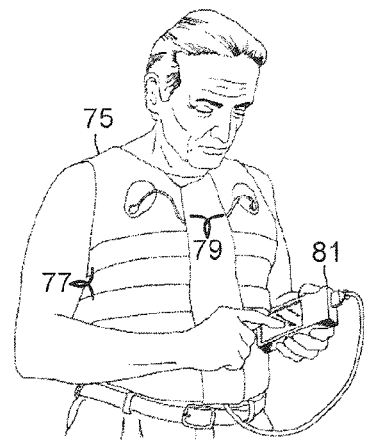
Figure 6C:
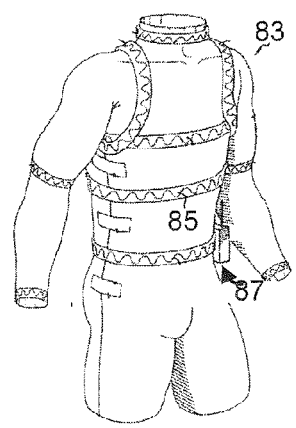
Figure 6D:
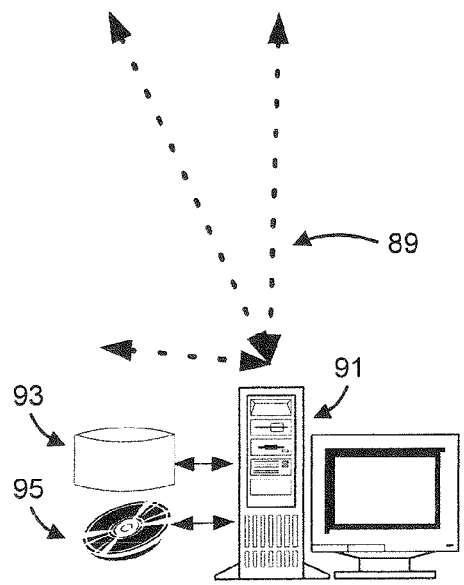
Figure 7:
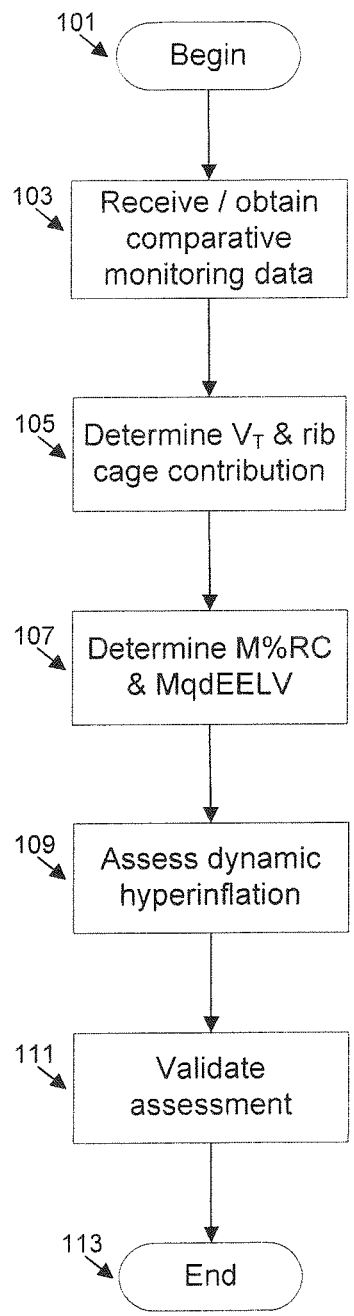

The present invention may be understood more fully by reference to the following detailed description of preferred embodiments of the present invention, illustrative examples of specific embodiments of the invention, and the appended figures in which:

FIGS. 1A1-1A4 illustrate aspects or respiratory anatomy;
FIGS. 1B-D illustrate aspects of respiratory function;
FIG. 2 illustrates calibrated respiratory data;
FIG. 3 illustrates the measurement of EELV in this invention;
FIG. 4 illustrates respiratory data from a normal patient;
FIG. 5 illustrates respiratory data from a patient with OPD;
FIG. 6 illustrates ambulatory monitoring devices; and
FIG. 7 illustrates methods of this invention.

5. DETAILED DESCRIPTION OF THE PREFERRED EMBODIMENTS

In the following, and in the application as a whole, headings are used for clarity and convenience only and without any intent to thereby alter or narrow the scope of the invention.

Dynamic Hyperinflation

This subsection provides brief descriptions of known aspects of pulmonary functioning that are useful for describing and supporting the present invention, in particular, aspects of respiratory mechanics and of respiratory volumes.

FIGS. 1A1-4 schematically illustrate relevant aspects of respiratory anatomy and mechanics. FIGS. 1A1 and 1A2 illustrate a side view and a cross section of a rib cage in inspiration. FIGS. 1A3 and 1A4 illustrate a side view and a cross section of a rib cage in expiration. Respiratory muscles acting directly on the rib cage are not illustrated; only diaphragm 23 is illustrated. Referring first to FIGS. 1A1 and 1A2, the respiratory muscles during inspiration act to lift and expand rib cage to position 11 and to lower the diaphragm to position 15. Referring now to FIGS. 1A3 and 1A4, during expiration, the respiratory muscles relax, and tissue elasticity and passive recoil allow the rib cage to contract to position 19 and the diaphragm to rise to position 21. Accordingly, measures of rib cage size (RC) increase during inspiration and decrease during expiration. This can be appreciated from the relation of the rib cage to equal length arrows 13 (FIGS. 1A1 and 1A3). Similarly, measures of abdomen (AB) size increase during inspiration and decrease during expiration. This can also be appreciated from the relation of the abdomen to equal length arrows 17 (FIGS. 1A2 and 1A4).

RC and AB size measurements (or either alone) can be linearly combined according to a two compartment breathing model in order to determine the various lung volumes, e.g., tidal volume, to within 5-10% of these volumes determined using a spirometer (a current measurement standard). Furthermore, comparing measurements of changes in rib cage and abdominal sizes to determined lung volumes, it can be determined how much of an individuals is due to rib cage motion and how much is due to diaphragmatic motion.

It is also known that, when inspirations and expirations occur at chest volumes in the central parts of their volume ranges, approximately midway from their minima to their maxima, a given change in lung volume requires a linear or proportionate amount of respiratory muscle effort (working against the elasticity of chest wall and lung). That is, in these volume ranges, the lung compliance is approximately constant so that minute ventilation (VE) increases approximately linearly and proportionately with respiratory muscle work. However, it can be appreciated from FIGS. 1A1 and 1A2 that when breathing occurs with chest and lung volumes in the upper part of their ranges, near their maxima, each breath requires that an already expanded rib cage 11 must be further expanded and an already lowered diaphragm 15 must be further lowered. This is mechanically and elastically disadvantageous; and each breath requires a non-linearly and disproportionately greater amount of respiratory muscle effort. Because of this decreasing lung compliance, greater and greater efforts and required to increase VE.

Figure 1C:
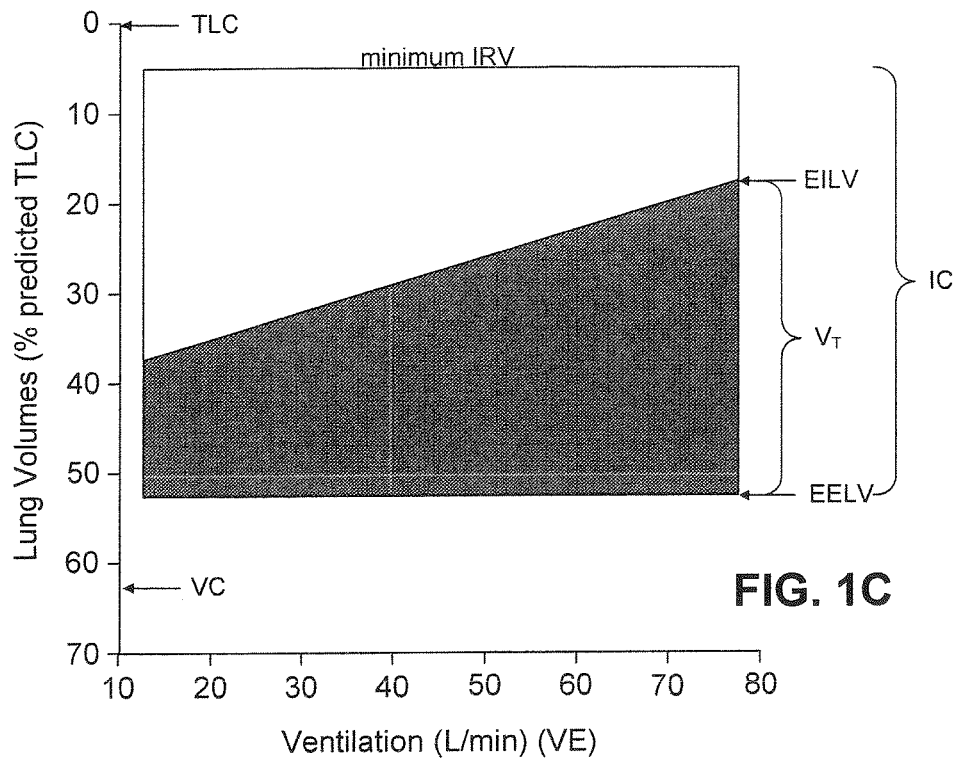

Next, FIGS. 1B-C illustrate schematically (and not to scale) relevant aspects of functional lung volumes. Referring first to FIG. 1B, total lung capacity (TLC) is the total volume of air in the lung; residual volume (RV) is the total volume of air remaining in the lung after a maximum expiratory effort; and function residual capacity (FRC) is the total volume of air remaining in the lung after a tidal expiration. (Alternately, TLC is often defined to include dead volume where there is no significant air exchange.) Measurement of these volumes commonly requires cumbersome techniques, for example, body plethysmography or gas dilution measurements.

The remaining lung volumes are more easily measured during routine breathing. Vital capacity (VC) is the expiratory volume from a maximal inspiration down to a maximal expiration. Normal breathing defines tidal end inspiratory lung volume (EILV) and tidal end expiratory lung volume (EELV), and the difference of these volumes defines tidal volume ($V_T$). Inspiratory capacity (IC), inspiratory reserve volume (IRV), and expiratory reserve volume can then be determined from VC and $V_T$ (either resting or exercise) as illustrated. In particular, IC is the inspiratory volume from a regular expiration up to a maximal inspiration, and will vary proportionately with the EELV.

FIG. 1C illustrates a normal subject's response to increased respiratory demand, such as occurs during exercise. The principal response is to increase $V_T$; the secondary response is to increase respiratory frequency, but usually only at high levels of respiratory demand. Because normal subjects have substantial IC and IRV, $V_T$ is easily increased by simply taking deeper inspirations without changing the EELV. Healthy subjects may also demonstrate a decreasing EELV as permitted by their VC and ERV. These inspiratory volume increases (and also expiratory volume increases) occur in the mid-range of TLC, e.g., between 20% and 60% of TLC. In this range, the respiratory system's compliance is largely constant, and increased respiratory effort leads to substantially linear and proportional increases in $V_T$ and VE.

Figure 1D:
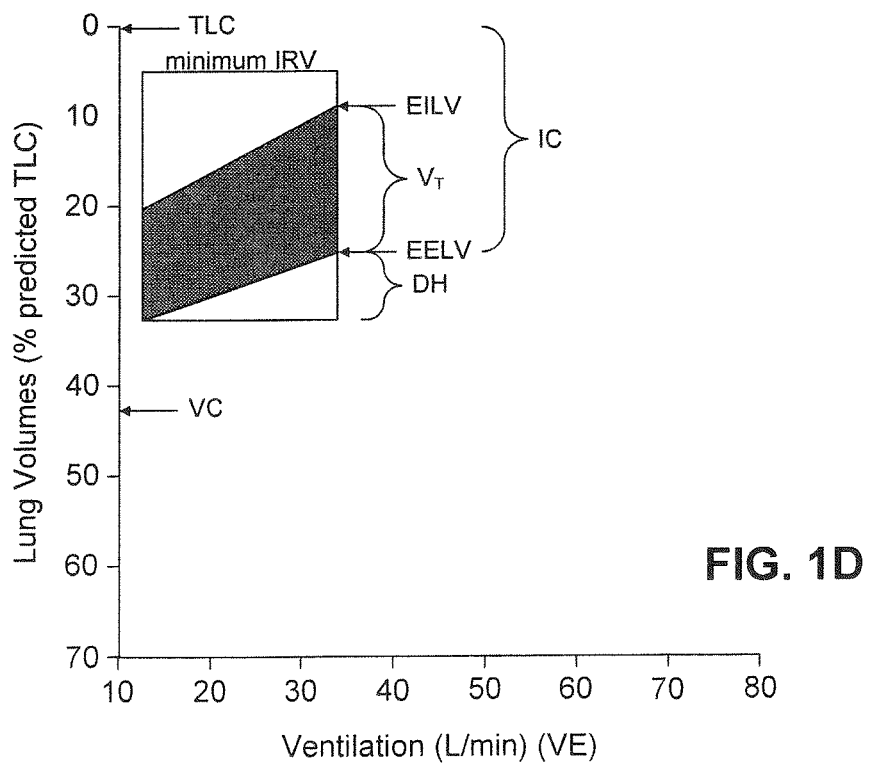

COPD, and other lung diseases leading to similar physiological defects, can dramatically compromise the normal respiratory response to increased respiratory demand. FIG. 1D illustrates a patient with advanced COPD. This patent's ventilatory reserve volumes are dramatically decreased by air flow limitations, incomplete expiratory lung, and static trapping of air not expired in lung segments with little of no ventilation in such patients leads. At rest (i.e. for ventilation near 10 L/min in FIG. 1D), approximately 70% of the lung is no longer available for active respiration and gas exchange. Only approximately 20% of TLC remains available as ventilatory reserve volumes, VC, IC, and ERV, which can be used to increase $V_T$ when needed. Also, as the active and ventilated lung volumes are displaced upward and closer to total lung capacity, respiratory compliance decreases. Increases in VE and $V_{T\,then}$ require greater and greater respiratory effort; and breathing becomes more and more tiring. OPD also increases to work of breathing also by increasing airway resistance. The patient illustrated in FIG. 1D therefore loses the normal subject's capability to substantially increase VE in response to respiratory demand (i.e., exercise).

In addition to being chronic, air trapping can also be acutely exacerbated and increased by various precipitating factors, e.g., a patient's attempts to increase VE as might occur during exercise. This can be seen by comparing the course of EELV and IC in FIGS. 1C and 1D. In a normal subject, FIG. 1C illustrates that EELV and IC are not substantially altered when VE increases. Thus, ventilatory residual volumes, or the lung volumes available for increased ventilation, are not compromised and remain available for increasing $V_T$. However, FIG. 1D illustrates that, in an OPD patient, EELV can further increase and IC can further decrease during even modest increases in VE. Here, ventilatory residual volumes are compromised and are not available for increasing $V_T$. In fact, it can be seen that the possible increase in $V_T$ is quite limited. However, it is also apparent from FIG. 1D that, if EELV and IC were substantially constant as VE increased, the patient's ventilatory reserve volumes, although already quite limited, are at least not further compromised and can be fully used to increase $V_T$ and thus VE. This additional effect of OPD, though to be caused by dynamically increased air trapping, is known as "dynamic hyperinflation" (DH). DH is dynamic because after precipitating factors cease, lung volumes return to their previous values.

The occurrence and extent of DH is variable. Determinants of DH include: baseline lung hyperinflation, expiratory flow limitation, ventilatory demand, and breathing pattern. The occurrence of DH is also variable. It be precipitated by different causes in different patients, for example, by exercise, by lung infection, by cold, by allergens and so forth. Although air trapping can range from 0.1 L or less, to 0.3 L, and to ≥1.0 L, absolute volumes must be compared to a patient's remaining lung function. Only 0.1-0.2 L of additional air-trapping can significantly compromise an individual already breathing with virtually no ventilatory reserve.

Thus DH acts like a further worsening of a patient's underlying disease because it further decreasing reserve volumes just when the patient needs them in order to increase ventilation. In these situations, notably during exercise, OPD patients can experiences increased sensations of dyspnea, breathlessness, and other discomforts. Therefore, tracking and managing DH in OPD patients can help preserve their functional capacity and quality of life.

Determination of Dynamic Hyperinflation

This subsection describes this invention's novel techniques and methods for non-invasively and unobtrusively determining dynamic hyperinflation. These are based on the discovery that the presence or absence of DH and an indication of its amount (volume) can be reliably determined by a finding specific pattern of joint changes in two specific respiratory parameters occurring during exercise or after other precipitating factor. On the other hand, DH cannot be reliably determined from only one of these parameters in isolation from the other.

The two significant parameters are known as "median % rib cage" ("M % RC") and "median cumulative change in end expiratory lung volume" ("MqdEELV"). These parameters and their measurement are now described. First, M % RC is a parameter available for each breath and measures the relative portion of a breath that is due to expansion and contraction of the rib cage. The remaining portion of the breath is due, as explained above, to contraction and relaxation of the diaphragm. FIG. 2 illustrates exemplary data. Graph 45 represents the tidal volumes ($V_T$) a series of breaths, each breath has a rising inspiratory portion and falling expiratory portion. Graph 47 represents concurrent relative changes in rib cage volumes, and graph 49 concurrent relative changes in abdomen volumes. For each breath, the % RC (percent RC) is the ratio of the amplitude in graph 47 to the corresponding amplitude in graph 45.

M % RC can be determined from respiratory measurements including tidal volume, or its equivalent, and rib cage size, or its equivalent, and is a weighted and/or normalized ratio of changes in rib cage size to the tidal volume. In preferred embodiments, respiratory data includes non-invasive, unobtrusive, moment-by-moment measurements of a rib cage size, known as RC, and an abdominal size, known as AB. Then, suitable weights α and β can be chosen so that tidal volume can be reliably determined from the formula:

$$V_T = \alpha * AB + \beta * RC \quad (1)$$

The % RC (percent RC) is then:

$$\% RC = \frac{\beta * RC}{V_T} \quad (2)$$

M % RC is a statistical median of % RC determined for breaths occurring during sequential 30 sec., or 1 min, or 2 min., or other periods. In other embodiments, $V_T$ can be alternately determined from a linear or non-linear function of AB and RC, and an alternate statistical measure, e.g., an average, can be used to represent values of % RC during sequential periods.

Next, finding MqdEELV requires prior determination of changes in EELV. Patterns of change in EELV are sufficient; the methods of this invention do not require absolute values of EELV. In preferred embodiments, changes in EELV are determined breath-by-breath by comparing the inspiratory volume of each breath to its expiratory volume. FIG. 3 illustrates a preferred method. Graph 31 schematically (not to scale) represents $V_T$ and includes four illustrative breaths, breaths 36, 40 and 42 being specifically identified. Breath 36 has inspiratory volume 35, which is measured from the end expiration of the previous breath to peak inspiration of breath 36, and expiratory volume 37, which is measured from peak inspiration of breath 36 to end expiration of breath 36. Since inspiratory volume 35 is greater than expiratory volume 37, breath 36 has caused EELV to increase by the difference in these volumes. EELV is represented by graph 33, and this graph depicts the EELV increase due to breath 36 by step 39. Breath 40 is similar: inspiratory volume 39 is greater than expiratory volume 41; and graph 33 represents this EELV increase by step 43.

Accordingly, graph 31 of EELV steps up by amount 39 at breath 36, by amount 43 at breath 40, and by a further amount at breath 42. Over the course of these three breaths, EELV cumulatively stepped up by amount 45. In actual respiratory data, EELV can both increase and decrease, and the cumulative change in EELV for a period of time cumulates all increases and decreases during that period. Finally, MqdEELV is the statistical median of the absolute value of a number of cumulative changes in EELV determinations made during sequential 30 sec., or 1 min, or 2 min., or other periods. In other embodiments, changes in MqdEELV can be determined by linear or non-linear combinations of inspiratory and expiratory volumes from two or more breaths; EELV changes can be cumulated by running averages and the like; and alternate statistical means, e.g., an average, can be used to characterize changes in EELV during sequential time periods.

Once these parameters are determined, the methods of this invention identify a patient who dynamically traps air in response to an inciting event (e.g., exercise, infection, etc.) because of an increasing MqdEELV together with a decreasing M % RC. Such patients are referred to herein as "+DH". In patients who do not dynamically trap air, referred to as −DH, MqdEELV and M % RC do not exhibit this pattern. In such patients, either MqdEELV decreases, or both MqdEELV and M % RC increase together.

FIGS. 4 and 5 illustrate these two patterns. In these figures, median values are determined for a time equal to approximately one and one-half time the vertical grid line spacing. FIG. 4 illustrates a healthy, −DH, subject who exhibits a normal pattern of joint changes in MqdEELV and M % RC during exercise. This patient has a significant exercise capability as evidence by a heart rate increase from approximately 70 beats per minute (bpm) to over 170 bpm. During the exercise period, the MqdEELV is stable, while the M % RC increases a small amount, from approximately 40% to approximately 50%. This pattern reflects a normal exercise response in which minute ventilation is increased by increasing tidal volume using rib cage muscles and the diaphragm in approximately equal proportions. No air trapping is evident. Another common normal pattern is a relatively small decrease in MqdEELV, because of somewhat large expirations, together with a relatively small increase in M % RC, because of relatively increased use of rib cage muscles. Also normals can exhibit a small increase in MqdEELV with changes in M % RC that are either not significant or are decreases.

FIG. 5 illustrates a subject with an obstructive pulmonary disease (here, COPD). First, this subject's exercise tolerance is decreased due to limitation in their ability to increase their minute ventilation. This is evidenced here by the only approximately 20 bpm increase in heart rate from an already elevated resting rate. Next, the MqdEELV significantly increases by approximately 140 ml; and the M % RC even more significantly decreases, falling from an approximately normal level above 40% to a much depressed level below 16%. These changes are consistent with dynamic air trapping. Increasing MqdEELV reflects increased air trapping and decreased volumes available for ventilation. A significantly decreasing M % RC reflects further physiologically significant dynamic air trapping in an already hyperinflated lung. Additional trapped air in a hyperinflated lung both limits rib cage contraction and further decreases an already abnormally decreased lung compliance. Both factors reduce the mechanical efficiency of the rib cage muscles, and the decreasing M % RC indicates that these muscles are now incapable of the extra effort to maintain ventilation.

Table 1 further illustrates how the novel pattern of an increasing MqdEELV and a decreasing M % RC separates +DH from −DH patients.

TABLE 1

| Parameter (base line - end exercise) | Patients without DH on exercise (−DH) | Patients with DH on exercise (+DH) | Difference (+DH minus −DH) |
| --- | --- | --- | --- |
| MqdEELV | −81.36 | 66.50 | −147.86 |
| M % RC | 1.09 | −12.50 | 13.59 |

This table summarizes data from a study of fifteen patients, some with DH confirmed by standard measurement techniques and some without DH also as confirmed by standard techniques. Changes in MqdEELV and M % RC were measured for each patient. It is readily apparent that +DH patients exhibit the pattern of increasing MqdEELV and decreasing M % RC, while −DH patients exhibit other patterns.

In further preferred embodiments, values of MqdEELV and M % RC are combined using a model developed according to statistical pattern recognition techniques for particular patient populations into a discriminant variables that clearly distinguish +DH from −DH in each population. Further, these discriminant variables can be chosen so that amount of DH (in ml) correlates with the value of the variables so that both presence and amount of DH can be determined. Other embodiments use models developed by other than statistical techniques and can incorporate further variables (such as intensity of exercise or of other inciting cause).

Preferred Systems and Methods of this Invention

Preferred systems and methods suitable for the practice of this invention are described next.

This invention can be practiced in many different patient monitoring environments as long as respiratory data is available from which at least moment-by-moment $V_T$ data and rib cage contribution to $V_T$ can be determined. For example, this invention can be practiced in hospital, clinic, or laboratory environments and use data from respiratory sensors available in these environments. Such sensors include, e.g., spirometeric measuring arrangements, body plethysmography, and the like and are often less portable, can limit or prevent patient motion, but offer greater measurement accuracies. These environments also often provide, e.g., exercise treadmills and the like which can provide graded stimuli to precipitate DH. This invention can also be practiced in a patient's day-to-day environment while the patient is performing day-to-day activities (referred to herein as "ambulatory environments"). In such embodiments, this invention usually processes data from respiratory sensors that are portable, light weight, non-invasive, and is arranged and configured so as not to limit patient motion or activity. Although practice in ambulatory environments is preferred and further described herein, this should not be understood to limit the broad applicability of this invention.

For ambulatory environments, respiratory sensors preferably respond to indicia of body sizes, such as lengths, circumferences, diameters, or geometrically similar measures of at least the rib cage and the abdominal and of their moment-by-moment changes during respiration. As already described, from rib cage and abdominal size measurements, moment-by-moment $V_T$ and rib cage contribution to $V_T$ can be determined. Such sensors (referred as "size sensors") at one or more additional torso or limb cross-sections can provide additional data responsive to cardiac or aortic pulsations, venous or arterial pulsations, and the like.

Size sensors can be based on diverse technologies, including magnetometers; strain gauges using magnetic, mechanical or optical means; optical techniques including interferometry; electrical impedance; surface electrical or magnetic activity; body plethysmography, ultrasonic and doppler measurements of body wall motions or body diameters; and so forth. Preferred size sensors are based on inductive plethysmographic (IP) technology, which is responsive to anatomic sizes by measuring the self-inductance of one or more conductive elements (metallic or non-metallic) arranged on the anatomic portion to be measured. Briefly, IP sensor self-inductance varies as its size changes in response to an underlying body part; the varying self-inductance is sensed by variable frequency oscillator/demodulator modules; these modules output digital signals responsive to oscillator frequencies and ultimately to sensor size. Respiratory measurements obtained by IP technology are routinely within 5-7% (or 10 s of ml) of measurements obtained by spirometry, a current clinical standard.

IP technology has been described in patent applications and issued patents assigned to the assignee of the present application including: U.S. Pat. Nos. 6,551,252; 6,413,225; 6,047,203; 6,341,504; 5,331,968; 5,301,678; 4,807,640; 4,373,534; and 4,834,209, and also U.S. application Ser. No. 10/822,260. All patents and published U.S. application cited herein are incorporated herein by reference in their entireties for all purposes.

Additional sensors are advantageous in order to record the context when DH is found to occur. For example, accelerometers mechanically coupled to a monitored patient can provide data reflecting activity level and posture; sensors for blood oxygen saturation can provide data reflecting any desaturation accompanying DH. Other sensors can provide data reflecting skin conductance, electrical impedances, temperature, sensors; ultrasound, and the like.

Respiratory and other sensor data is conveyed from the monitored patient to processing devices, or computers, or computer systems for processing and analysis by programmed implementations of this invention's methods. If patients are constrained, sensors can be linked directly to processing systems, e.g., by cable. If patients are unconstrained as in ambulatory environments, it is preferable that a portable processing device or computer (referred to as a "portable data unit" or "PDU") carried by a subject receive sensor data. In certain embodiments, the PDU also temporarily stores and/or transmits it to remote computers for analysis. In an ambulatory environment, data transmission should not limit a subject and can be by, e.g., wireless transmission, or physical transport of computer readable media, or the like. In other embodiments, the PDU also perform the methods of this invention.

For ambulatory applications, respiratory and other sensors are preferably configured unobtrusively and comfortably on the patient so as not to substantially limit motion or activity. For example, sensors can be configured into one or more wearable items, e.g., shirts, jackets, bands, patches, and the like. FIGS. 6A-C illustrate exemplary ambulatory monitoring systems having sensors configured into wearable items.

The subject of FIG. 6A is actively exercising unconstrained by concurrent monitoring with a single chest band 71 and PDU 73 configured as a wrist watch. The single band preferably incorporates a size sensor sensitive to respiration and can also incorporate accelerometers, ECG sensors, temperature sensors, and so forth. FIG. 6B illustrates shirt-like garment 75 having several types of sensors, including two (or more) size sensors 77 preferably sensitive to rib cage (RC) and abdomen (AB) sizes, two ECG leads, and optionally additional sensors (not illustrated). Here, PDU 81 can displays data and accept user input. FIG. 6C illustrates a body-suit-like garment 83 equipped with a more extensive array of size sensors 85 for measuring respiration rate and volume, venous and arterial pulsations, cardiac pulsations, individual lung function, and the like. Here, PDU 87 is attached to the garment and retrieves and wirelessly transmits sensor data to storage and analysis systems. Monitoring garments and systems are available from VivoMetrics, Inc., Ventura, Calif.

Sensor data can be partially or wholly processed by a processing device in the PDU. In certain embodiments, processed and/or raw data is also transmitted to a remote computer system. FIG. 6D illustrates an exemplary analysis system including PC-type or workstation-type computer 91 with an attached monitor for viewing unprocessed and processing sensor data. Data is 89 conveyed to system 91 by, e.g., wireless connection, physical transfer, or wired connection. Local or remote online computer readable memory 93 and removable computer readable memories 95 (e.g., optical ROM) holds unprocessed and/or processed data and/or programs, and the like.

The methods of this invention are generally performed on a computer or other processing device. Accordingly, these methods are programmed in a convenient computer language, such as assembly language, C, or C++, compiled into an executable form and stored on a computer readable medium for loading into a program memory of a computer or the configuration registers of a programmable device, or the like. FIG. 7 illustrates an exemplary implementation of these methods. These illustrated steps can be repeated on demand, or intermittently, or periodically to make multiple DH assessments.

After beginning at step 101, next step 103 measures and/or retrieves and/or inputs current monitoring data and optionally comparative measurement data. DH is additional hyperinflation acutely superimposed on chronic, baseline (BL) hyperinflation. To assess the degree or severity of a current bout of DH, it is therefore advantageous to have available comparative data that measures of the BL hyperinflation. Comparative data can include values or combinations of MqdEELV and M % RC during past bouts of DH, statistical distributions of multiple observations of MqdEELV and M % RC; the values of MqdEELV and M % RC resulting from specific precipitation factors, the amount of air retained, and the like.

Should the input data include RC and AB size measurements, step 105 next extracts tidal volume ($V_T$) and the rib cage contribution to tidal volume from these raw methods accordingly to methods known for IP. Step 107 perform implementations of the previously methods for finding M % RC and MqdEELV. Finally, step 109 assesses DH, its presence or absence and optionally its amount or volume, from the determined M % RC and MqdEELV parameters accordingly to the discrimination already described. The severity of DH can be estimated from the increases in lung volume or other measured in view of past values provided in the comparative data.

Validation step 111 is optional but preferred to insure and/or improve the reliability of DH assessments. In one simple alternative, single measurements the M % RC and MqdEELV parameters are made from sufficiently long measurement periods, e.g., at least 30 sec, or at least 60 sec, or at least 120 sec. long or longer. In another alternative, DH assessment uses M % RC and MqdEELV values that are determined by statistically combining two or more independent measurements of these parameters. In a further alternative, a final DH assessment is determined by statistically combining values from two or more independent episodes of DH precipitated by separate occurrences of a precipitating factor, e.g., exercise. Values can be combined using modes, medians, averages, and the like in order to statistically improve accuracies and limit errors. Prior DH episodes can be provided in the comparative data.

The invention described and claimed herein is not to be limited in scope by the preferred embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

A number of references are cited herein, the entire disclosures of which are incorporated herein, in their entirety, by reference for all purposes. Further, none of these references, regardless of how characterized above, is admitted as prior to the invention of the subject matter claimed herein.

What is claimed is:

1. A computer-implemented method suitable for use during exercise activities for assessing respiratory data in a monitored subject, the method comprising:
   monitoring respiration of the subject with a physiological monitoring system, wherein the physiological monitoring system comprises a magnetometer for collecting respiratory data;
   using a processor to determine a tidal volume of the subject based on the respiratory data;
   using the processor to determine a first parameter indicative of the relative contribution of expansion and contraction of the subject's rib cage to the subject's tidal volume;
   using the processor to determine a second parameter indicative of median cumulative changes in end-expiratory lung volume; and
   assessing respiratory data in the subject in dependence on the first and second parameters.

2. The computer-implemented method of claim 1, wherein the monitoring respiration of the subject is performed during a subject monitoring period, and wherein the first and second parameters are determined from received respiratory data from the same subject monitoring period.

3. The computer-implemented method of claim 2, wherein the respiratory data of the subject monitoring period is compared with a previous subject monitoring period.

4. The computer-implemented method of claim 1, wherein using a processor to determine the second parameter comprises:
   determining a breath-by-breath change in expiratory lung volume;
   determining a cumulative change in expiratory lung volume in dependence on a plurality of consecutive breath-by-breath changes in expiratory lung volume; and
   determining the median cumulative changes in end-expiratory lung volume parameter in dependence on the absolute values of a plurality of cumulative changes in expiratory lung volumes.

5. The computer-implemented method of claim 4, wherein determination of the breath-by-breath change in expiratory lung volume comprises subtracting the expiratory volume of the breath from the inspiratory volume of the breath.

6. The computer-implemented method of claim 1, further comprising gathering data relating to a rib cage size and an abdomen size of the subject,
   determining a lung volume parameter by linearly combining the rib cage size and the abdomen size; and
   determining tidal volume of the subject in dependence on a difference of the lung volume parameter at the end of inspiration and the lung volume parameter at the end of a following expiration.

7. The computer-implemented method of claim 1, wherein determining the first parameter comprises dividing respiratory volume during expansion of the subject's rib cage by the subject's tidal volume.

8. The computer-implemented method of claim 1, wherein the respiratory data comprises a rib cage size of the subject, and wherein respiratory volumes during rib cage expansion and contraction are determined in dependence on the rib cage size.

9. The method of claim 1, wherein the subject performs normal daily activities during the monitoring period.

10. A computer for assessing respiratory data in a subject monitored during exercise with a physiological monitoring system, wherein the physiological monitoring system comprises a magnetometer for collecting respiratory data, the computer comprising:
- a processor; and
- a computer-readable memory operatively coupled to the processor, wherein the processor is configured to:
- determine a tidal volume of the subject based on the respiratory data;
- determine a first parameter indicative of the relative contribution of expansion and contraction of the subject's rib cage to the subject's tidal volume;
- determine a second parameter indicative of median cumulative changes in end-expiratory lung volume; and
- assess respiratory data in the subject in dependence on the first and second parameters.

11. The computer of claim 10, wherein the processor and the memory are sized and configured to allow the computer to be easily carried by the subject.

12. A portable monitoring system for assessing respiratory data in a subject monitored during exercise with a physiological monitoring system, wherein the physiological monitoring system comprises a magnetometer for collecting respiratory data, the portable monitoring system comprising:
- a wearable item comprising one or more sensors that provide data comprising sizes at one or more selected positions on the subject's torso, the selected positions including one or more positions on the rib cage and one or more positions on the abdomen, the selected positions being selected so that the torso sizes change with respiration;
- a portable data unit operably linked to the sensors, the portable data unit comprising a processing device and a computer memory operably linked to the processing device and configured with computer instructions that cause the processor to perform the steps of:
- determining a tidal volume of the subject based on the respiratory data;
- determining a first parameter indicative of the relative contribution of expansion and contraction of the subject's rib cage to the subject's tidal volume;
- determining a second parameter indicative of median cumulative changes in end-expiratory lung volume; and
- assessing respiratory data in the subject in dependence on the first and second parameters.

13. The portable monitoring system of claim 12, wherein the wearable item is selected from the group consisting of a garment, a shirt, or a band.

14. The portable monitoring system of claim 12, wherein the portable data unit is housed so as to be carried on the wearable item worn by the subject.

15. The portable monitoring system of claim 12, wherein the sensors comprise one or more inductive plethysmographic sensors or one or more posture and/or activity sensors.

16. The portable system of claim 12, wherein the portable data unit stores data on a removable computer-readable memory.

17. The portable monitoring system of claim 12, wherein the portable data unit wirelessly transmits data to a remote computer.

18. The portable monitoring system of claim 12, wherein the subject performs normal daily activities during the monitoring period.

* * * * *